US010517340B2

(12) United States Patent
Ladaev

(10) Patent No.: US 10,517,340 B2
(45) Date of Patent: Dec. 31, 2019

(54) GARMENT SLEEVE WITH PARTIAL ZIPPER SEAM

(71) Applicant: Rafael Ladaev, Kiryat Malachi (IL)

(72) Inventor: Rafael Ladaev, Kiryat Malachi (IL)

( * ) Notice: Subject to any disclaimer, the term of this patent is extended or adjusted under 35 U.S.C. 154(b) by 0 days.

(21) Appl. No.: 15/038,460

(22) PCT Filed: Feb. 3, 2015

(86) PCT No.: PCT/IL2015/050116
§ 371 (c)(1),
(2) Date: May 22, 2016

(87) PCT Pub. No.: WO2015/118528
PCT Pub. Date: Aug. 13, 2015

(65) Prior Publication Data
US 2016/0345647 A1    Dec. 1, 2016

Related U.S. Application Data

(60) Provisional application No. 61/936,367, filed on Feb. 6, 2014.

(51) Int. Cl.
| | |
|---|---|
| *A41D 27/10* | (2006.01) |
| *A41D 27/28* | (2006.01) |
| *A41B 7/02* | (2006.01) |
| *A41D 1/00* | (2018.01) |
| *A44B 1/00* | (2006.01) |
| *A61B 5/022* | (2006.01) |

(52) U.S. Cl.
CPC .............. *A41D 27/285* (2013.01); *A41B 7/02* (2013.01); *A41D 1/00* (2013.01); *A41D 27/10* (2013.01); *A44B 1/00* (2013.01); *A61B 5/02233* (2013.01); *A41D 2300/32* (2013.01); *A41D 2300/322* (2013.01); *A41D 2300/324* (2013.01)

(58) Field of Classification Search
CPC .... A41B 7/02; A41B 7/06; A41B 7/08; A41B 7/10; A41B 5/00; A41B 11/06; A41D 27/285; A41D 1/00
USPC ........................................................ 2/270
See application file for complete search history.

(56) References Cited

U.S. PATENT DOCUMENTS

| | | | | |
|---|---|---|---|---|
| 2,145,118 A | * | 1/1939 | Knoess ................ | A44B 19/262 24/429 |
| 2,715,226 A | * | 8/1955 | Weiner ................... | A41D 27/28 2/79 |
| 5,033,126 A | * | 7/1991 | Wruck ..................... | A41D 1/08 2/22 |
| 5,822,802 A | * | 10/1998 | Chou .................. | A41D 13/1254 2/227 |
| 6,148,444 A | * | 11/2000 | Holmes .............. | A41D 13/1245 2/114 |

(Continued)

*Primary Examiner* — Timothy K Trieu
(74) *Attorney, Agent, or Firm* — Mark M. Friedman

(57) ABSTRACT

A garment sleeve having a proximal shoulder end coupled to an armscye of the garment, and a distal, cuff end, terminating at a cuff, the garment sleeve including: (a) a seam running from the armscye to the cuff the seam being joined at least at the shoulder end and at the cuff end; (b) a non-separating zipper including;—(i) teeth, and (ii) at least one slider adapted to reversibly couple the teeth, at least partially, between the shoulder end and the cuff end; the non-separating zipper operationally coupled proximate to the shoulder end of the seam and proximate to the cuff end of the seam.

13 Claims, 6 Drawing Sheets

(56) References Cited

U.S. PATENT DOCUMENTS

| | | | | |
|---|---|---|---|---|
| D635,334 S | * | 4/2011 | Eckman | D2/847 |
| 2007/0199127 A1 | * | 8/2007 | Coronado | A41D 13/1245 2/69 |
| 2014/0026289 A1 | * | 1/2014 | Schulties | A41D 13/1245 2/114 |

* cited by examiner

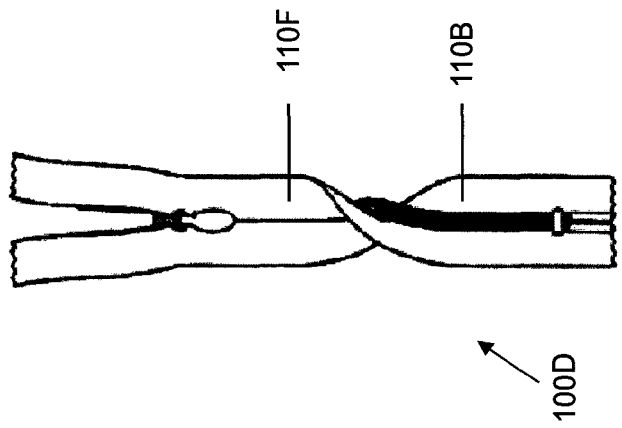
FIG. 1D
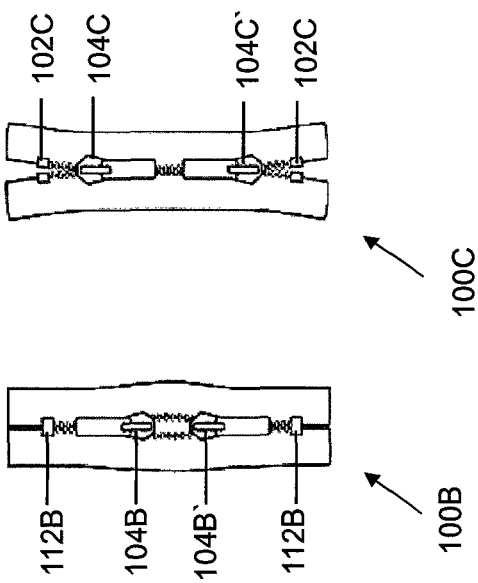
FIG. 1C
FIG. 1B
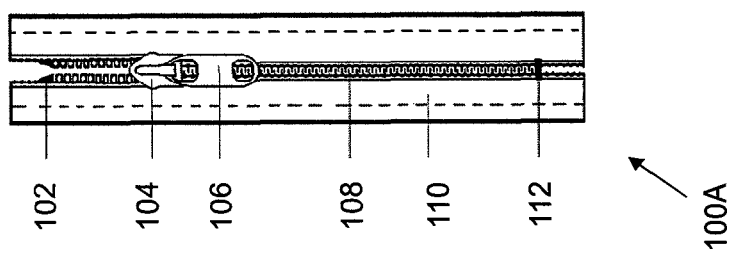
FIG. 1A

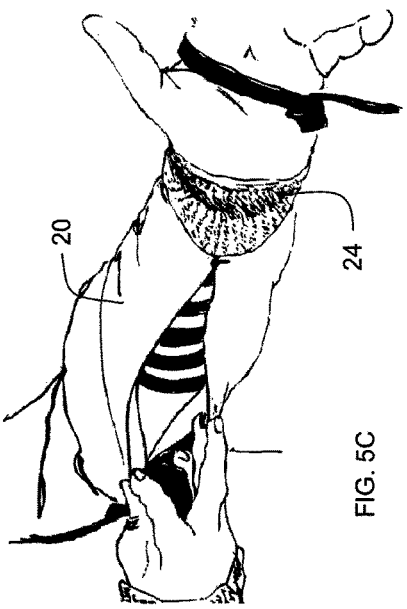
FIG. 5A
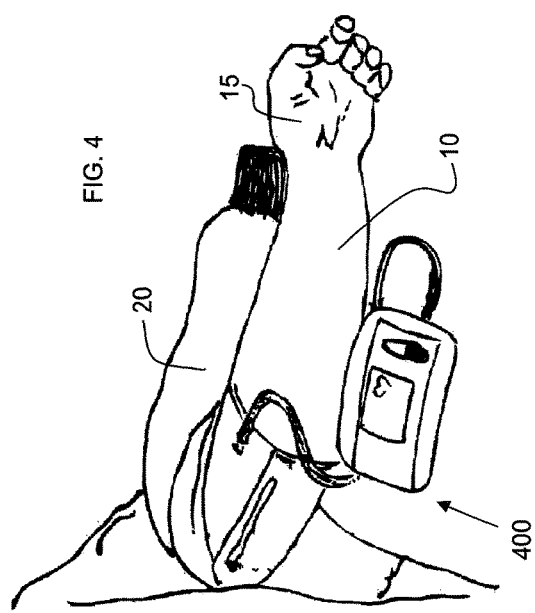
FIG. 4
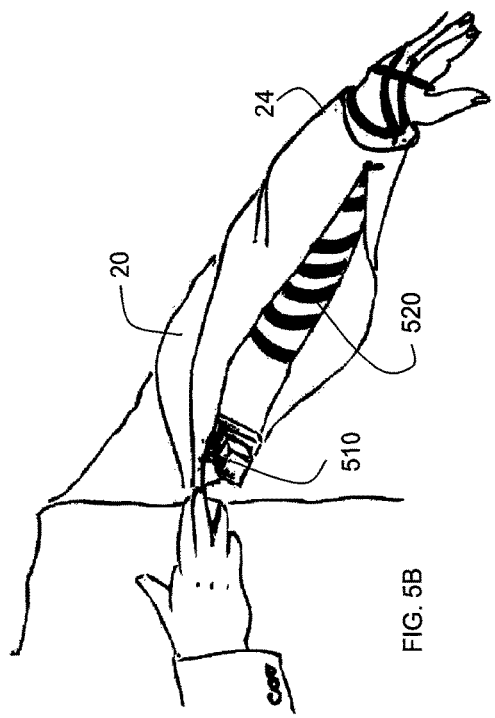
FIG. 5B
FIG. 5C

GARMENT SLEEVE WITH PARTIAL ZIPPER SEAM

FIELD OF THE INVENTION

The invention is in the field of clothing technology.

BACKGROUND OF THE INVENTION

While wearing a long-sleeved upper garment, there are instances in which physical access to an arm, including the upper arm, is necessary. For example, patients who take frequent blood tests, or a Jewish man, who every day wears an arm phylactery, known as Tefillin, on the upper arm. Such arm access can be cumbersome, as one has to remove the garment's sleeve by pulling the sleeve completely off of his arm. While wearing the Tefillin, inserting the arm back into the sleeve is even more difficult than was sleeve removal.

Prior art includes a sleeve with a zipper. To access an arm, one unfastens the zipper starting from the end of the sleeve by the wrist until the upper arm, thereby freeing the arm from the sleeve along the entire length of the zipper. To re-attire the sleeve, one fastens the zipper, thereby wrapping the arm with the sleeve. When the zipper is fastened, the zipper's pull tab is located at the end of the sleeve near the wrist. Both the zipper and its pull tab are usually visible or conspicuous. Such visibility reduces the aesthetic appeal of the garment, especially for formal garments such as suit jackets and sport jackets.

SUMMARY OF THE INVENTION

There is provided a garment enabled with easy access to the arm, including the upper arm, with an enabling mechanism that is non-conspicuous or non-visible.

According to the present invention there is provided a garment sleeve having a proximal, shoulder end coupled to an armscye of the garment, and a distal, cuff end, terminating at a cuff, the garment sleeve including: (a) a seam running from the armscye to the cuff, the seam being joined at least at the shoulder end and at the cuff end; (b) a non-separating zipper including: (i) teeth, and (ii) at least one slider adapted to reversibly couple the teeth, at least, partially, between the shoulder end and the cuff end; the non-separating zipper operationally coupled proximate to the shoulder end of the seam and proximate to the cuff end of the seam.

According to further features in preferred embodiments of the invention described below the non-separating zipper is an it invisible zipper, such that when the invisible non-separating zipper is in a closed state, the garment sleeve appears to have a single contiguous sewn seam from the armscye to the cuff.

According to still further features in the described preferred embodiments the zipper further include a tab, coupled to the at least one slider, herein in the closed state the tab is adapted t be recessed in such a manner so as to not be visible.

According to still further features the zipper further includes a second slider, the second slider, in conjunction with the at least one slider adapted to reversibly open at least a portion of the non-separating zipper.

According to still further features the at least one slider and the second slider are arranged in a head-to-head configuration on the non-separating zipper.

According to still further features the at least one slider and the second slider are arranged in a tail-to-tail configuration on the non-separating zipper.

According to still further features the seam join at the shoulder end, is about one centimeter in length or about two centimeters in length or about three centimeters in length.

According to still further features the seam join at the cuff end, is about one centimeter in length or about two centimeters in length or about three centimeters in length.

According to still further features the zipper further includes a tab, coupled to the at least one slider, the tab having a body length of about one centimeter.

According to another embodiment there is provided a garment sleeve having a proximal, shoulder end coupled to an armscye of the garment, and a distal, cuff end, terminating at a cuff, the garment sleeve including: (a) a seam running from the armscye to the cuff, the seam being joined at least at the shoulder end and at the cuff end; (b) a fabric fastener, adapted to be unfastened and refastened, the fabric fastener operationally coupled proximate to the shoulder end of the seam and proximate to the cuff end of the seam.

According to further features the fabric fastener is selected from one of: a zipper a hook-and-loop fastener, press studs, buttons, clips and any combination thereof.

This document references terms that are used consistently or interchangeably herein. These terms, including variations thereof, are as follows.

In sewing, the armscye is the armhole, the fabric edge to which the sleeve is sewn. The length of the armscye is the total length of this edge; the width is the distance across the hole at the widest point.

In sewing, a seam is the join where two or more layers of fabric, leather, or other materials are held together with stitches. As used herein, the term "seam" is used in the general sense as referring to the join of two or more layers or ends of fabric. Specifically, the seam in the present invention is partially sewn and partially formed by a zipper. The zipper may be a visible zipper or an invisible zipper. When an invisible zipper is used, and the zipper is closed, the entire length of the seam has the appearance of a sewn seam.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Various embodiments are herein described, by way of example only, with reference to the accompanying drawings, wherein:

FIG. 1A-D depict various types and configurations of zippers;

FIG. 4 is a first exemplary use case of the immediate invention;

FIG. 5A-C is a second exemplary use case of the immediate invention;

DESCRIPTION OF THE PREFERRED EMBODIMENTS

The principles and operation of a zipper sleeve according to the present invention may be better understood with reference to the draw and the accompanying description.

Referring now to the drawn FIGS. 1A to 1D depict various types and configurations of zippers. 1A illustrate a non-separating zipper 100A. The components of the zipper include: Two Top Stop mea filers 102 affixed to the top end of a zipper, to prevent the slider from coming off the chain. A Slider, or slider head, 104 is the member that moves up and down the chain in order to open or close the zipper. A Pull Tab, Tab or Puller 106 is the part of the slider that is held but the user in ordered to move the slider up or down. A Chain or Zipper Teeth 108 is the continuous piece that is formed when both halves of a zipper are coupled together by the slider 104. The fabric part of the zipper is referred to as Tape 110. A Bottom Stop 112 is a member that is affixed to the bottom end of a non-separating zipper, to prevent further movement of the slider.

Various types of zippers are known in the art. Only non-separating zippers are germane to the immediate invention. The zippers referred to herein are not only non-separating on one end, but rather they are non-separating on both ends. That is to say that the zipper is closed in by material on both ends.

There are visible and invisible types of zippers. Within the category of non-separating zippers (both visible and invisible zippers) there are single-slide zippers and double slide zippers. Single slide zippers can open in the proximal-distal direction (i.e. open from near to the body or head in the direction away from the body or head) or in the opposite, distal-proximal, direction (i.e. towards the body or head). Double slider zippers can either be in a head-to-head configurations or a tail-to-tail configuration. With a head to head configuration, the sliders are pulled away from each other to open the zipper teeth. With the tail to tail configuration, each slider opens from one of the extreme edges of the zipper, until the one slider comes into contact with the other slider.

FIG. 1B depicts a visible, non-separating, head-to-head zipper 100B. A head-to-head zipper includes two sliders and tabs 104B and 104B'. Each end of the zipper terminates in a Stop 112B.

FIG. 1C depicts a visible, non-separating, tail-to-tail zipper 100C. Zipper 100C includes a first slider and tab 104C and a second slider and tab 104C. Each end of the zipper 100C terminates in Two Top Stop members 102C.

FIG. 1D depicts an invisible, non-separating zipper 100D. In FIG. 1D, the tape front is referenced 110F and the tape back is referenced 110B. When the invisible zipper is in a closed state, the join between the two pieces of fabric, the tape fronts, appears as a regular seam, without the teeth of the zipper being visible.

Figure 2:
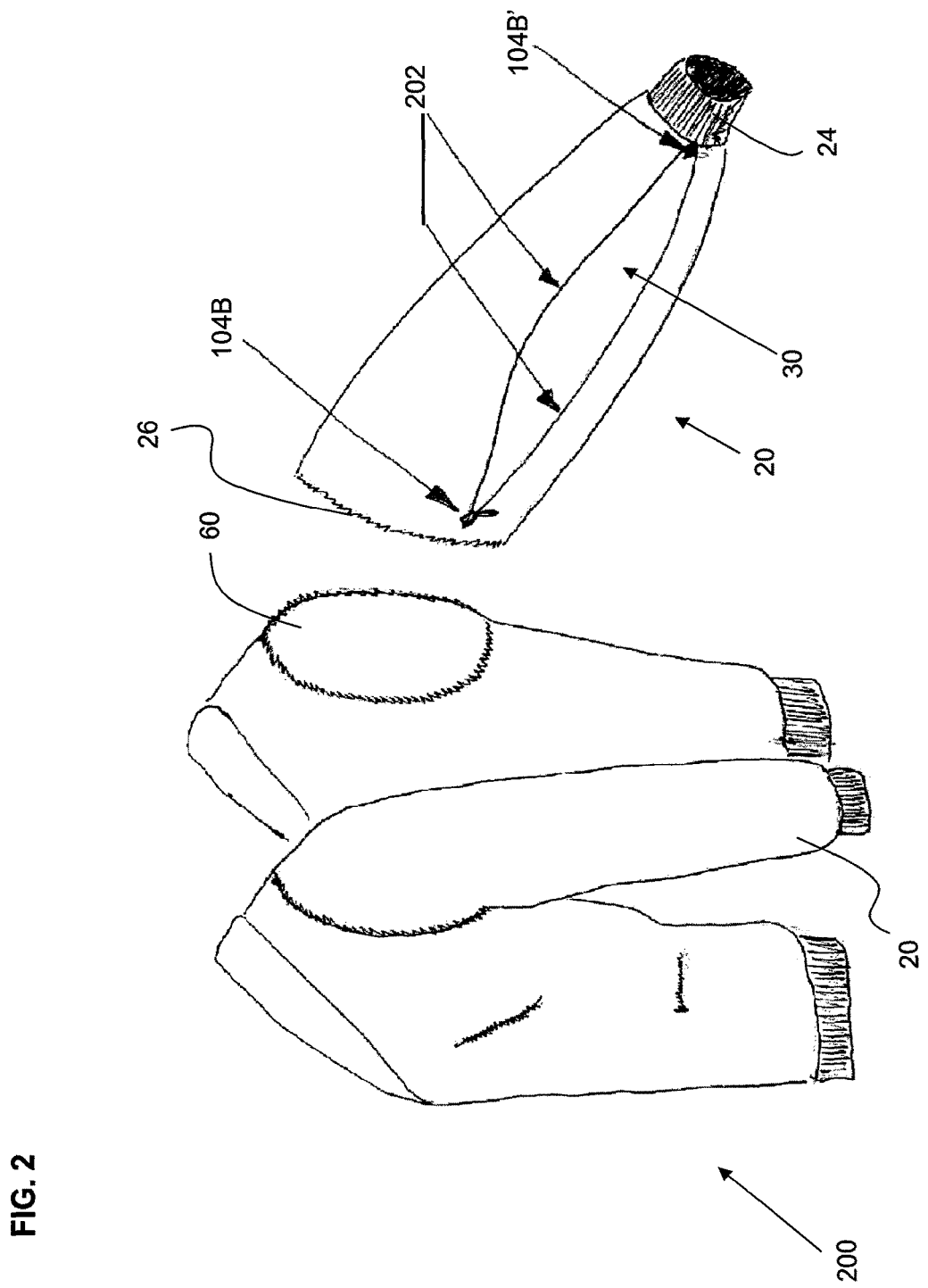
FIG. 2 is a partial of an exemplary coat with a sleeve in an attached view and the coat with the sleeve in a detached view, with an exemplary zipper in an open state.

FIG. 2 depicts a partial view of an exemplary coat or suit jacket 200 with garment sleeve 20 attached to the garment ("attached view") and a second view of the garment with sleeve 20 detached there-from ("detached view") with an exemplary zipper 202 in an open state. An armscye 60 is visible in the detached view. The seam of the join between the armscye and the sleeve is clearly visible in the attached view. A shoulder end/edge 26 of the garment sleeve is clearly visible in the detached view of the garment. Exemplarily, the zipper of the sleeve 20 is a head-to-head zipper configuration 100B with a first slide 104B open to near the shoulder edge and a second slide 104B' (using the reference characters from FIG. 1B) open to near a sleeve cuff 24. A zipper opening 30 is clearly visible in the detached view.

Figure 3A:
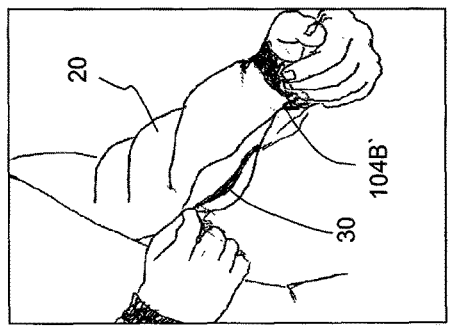
FIG. 3A is a front view of an exemplary garment with seams running on the undersides of the garment sleeves.
Figure 3B:
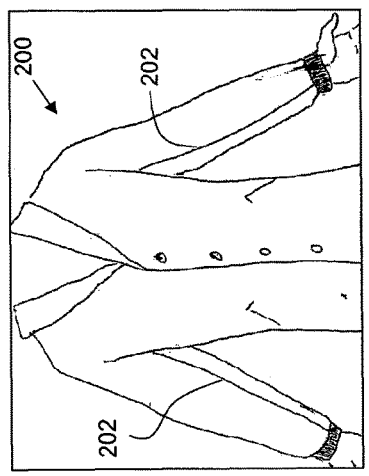
FIG. 3B is a pictorial view of the zipper in a partially opened state.

FIG. 3A depicts an exemplary garment 200 with seams 202 running on the undersides of the garment sleeves 20. Each seam 202 is partially sewn proximal to armscye 60 and proximal to cuff 24. An invisible zipper (e.g. zipper 100B) forms the rest of seam 202. FIG. 3B depicts the zipper in a partially opened state. The zipper configuration depicted in FIGS. 3A-3D is a head-to-head type zipper, similar to zipper 100B in FIG. 1B. The zipper is opened to the full extent on the cuff end and is in the process of being opened further towards the shoulder end 26 of the sleeve. It is of special note that even when the zipper is fully open on the cuff end, the cuff of the sleeve remains intact and joined along the seam.

Figure 3D:
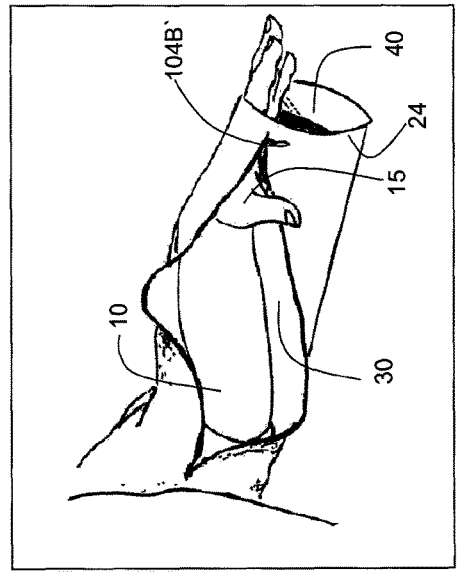
FIG. 3D is a pictorial view of a hand of the wearer partially retracted through the cuff hole and zipper opening of the sleeve.
Figure 3C:
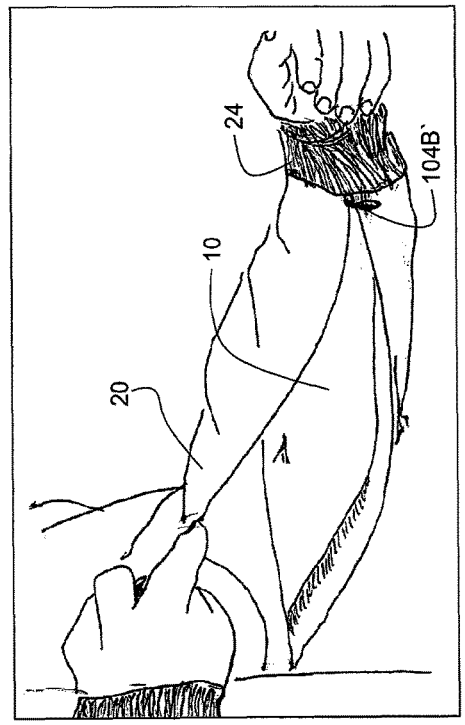
FIG. 3C is a pictorial view of the zipper in a fully opened state.

FIG. 3C depicts the zipper of the garment sleeve in a fully opened state. The naked arm 10 of the wearer is visible. Limited access is now afforded to the naked arm. In order to afford full access to the arm of the wearer, the arm can be retracted through the cuff hole 40 and zipper opening 30. FIG. 3D depicts a hand 15 of the wearer partially retracted through cuff hole 40 and zipper opening 30 of the sleeve.

FIG. 4 depicts an exemplary use of the sleeve zipper. In the pictorial depiction of FIG. 4, arm 10 of the wearer is fully extracted from the sleeve 20, through the zipper opening 30, and accessible, exemplarily, for applying a blood pressure machine 400 to the exposed and naked upper arm. In the depicted example, the arm remains outside of the sleeve for the duration of the exemplary procedure (blood pressure monitoring).

FIGS. 5A-5C depict a second use case. The use of Teffilin (arm phylactery) by Jewish men has been briefly discussed above and will now be discussed in further detail, with reference to the Figures. FIG. 5A depicts a classic arm phylactery 500 bound about the arm of a wearer. The arm phylactery 500 is comprised of a leather box-like construction 510 ("box") which is secured to the bicep of the upper arm by a length of leather strap 520 about 2-3 meters long. The remaining length of strap 510 is then wound around the arm 10 of the wearer (seven times, below the elbow) and tied in a specific manner about the hand and fingers of the wearer. The positioning of box 500 is specific, and there exists a stipulation that the box and strap be in direct contact with the naked flesh of the arm and hand. The Teffilin are generally worn on the left arm (of a right-handed individual) during the weekday morning prayers which have a length of between 30 and 90 minutes on average.

Access to the arm, including the upper arm, presents various challenges when wearing long-sleeved clothing such as a long-sleeved shirt, a suit jacket, sweater, windbreaker, winter jacket and the like. The current practice is to roll up a shirt sleeve above the bicep, and attach the Teffilin. Once correctly attached, some choose to leave the sleeve as is while others prefer to unroll the sleeve over the Tefillin. If an outer-wear garment is worn (e.g. suit jacket, sweater, windbreaker etc.) then at least the presenting arm is removed from the outer-garment sleeve. As with the long-sleeved shirt, some prefer to return the adorned arm into the outer-garment sleeve while other prefer to leave the arm exposed for the duration of the prayers.

Unrolling the sleeve or returning the adorned arm to the outer-garment sleeve is generally a cumbersome, complex and potentially uncomfortable procedure, depending on how tight the sleeve is fit. On the other hand, leaving the sleeve rolled up high on the upper arm and/or having the outer-garment sleeve hanging off the wearer is also uncomfortable and often unwieldy. In addition, when the weather is cold and/or the wearer is in an exposed environment (e.g. in the army on field exercises which often include overnight stays in the field), exposing a naked arm for any duration of time can be very uncomfortable. Therefore, with the immediate invention, a wearer can simply unzip the zipper of the sleeve (see FIGS. 3D and 3C), remove the hand and arm from the sleeve (see FIGS. 3D and 4) and don the Tefillin. Thereafter, the hand can be replaced in the sleeve, as depicted in FIG. 5B and the zipper closed over box 500 and strap 520, as depicted in FIG. 5C.

Figure 6B:
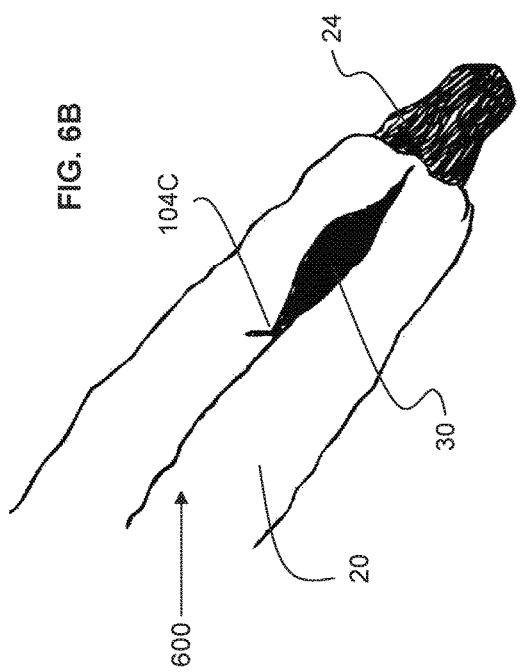
FIG. 6A-D is a second configuration of the immediate invention.
Figure 6D:
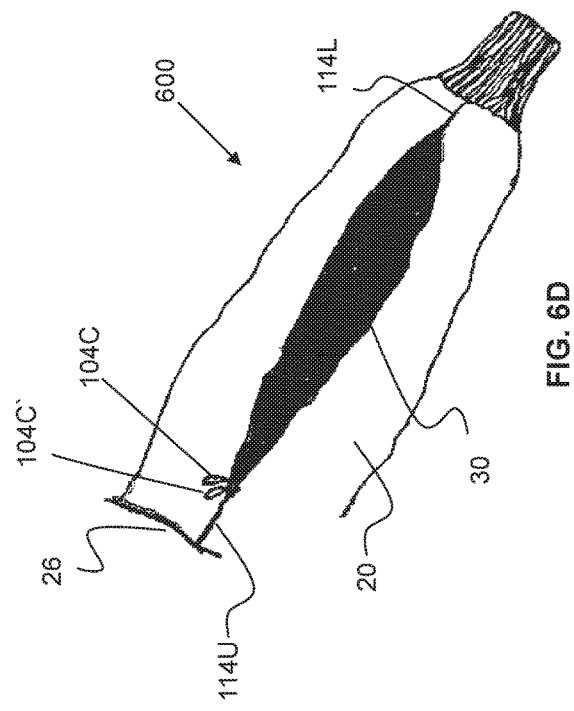
Figure 6A:
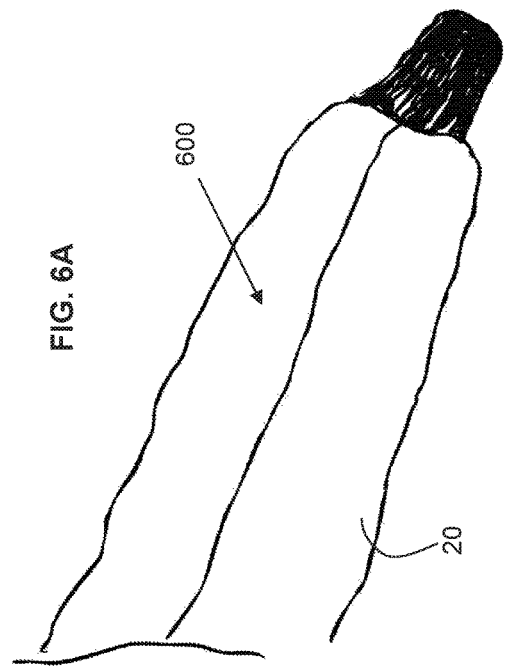

Another possible configuration is shown in FIGS. 6A-6D. FIG. 6A depicts a jacket sleeve 20 including a non-separating invisible zipper 600. In the Figure, the zipper is in a closed state. The chain/teeth of the zipper are invisible due to the type of invisible zipper used which is similar to zipper 100D depicted in FIG. 1D. The double slider configuration of the zipper is similar to tail-to-tail configuration of zipper 100C depicted in FIG. 1C. In the preferred embodiment, both the sliders and tabs are hidden in recesses of the fabric. In preferred embodiments, the tab is small and inconspicuous, so as to be concealed easily. For example, the tab may be length of a fingertip, i.e. about a centimeter long. When in the depicted closed state the sleeve appears to leave single, contiguous, sewn seam from the armscye to the cuff of the sleeve. In other words the sleeve appears to be a regular sleeve with a regular seam.

FIG. 6B depicts sleeve 20 with zipper 600 partially open. The zipper is open from near the cuff in the direction of the shoulder end. Zipper opening 30 is revealed by drawing slider and tab 104C (using the reference of FIG. 1C) approximately a third of the length of the zipper away from cuff 24. The second slider 104C' is not shown in FIG. 6B.

Figure 6C:
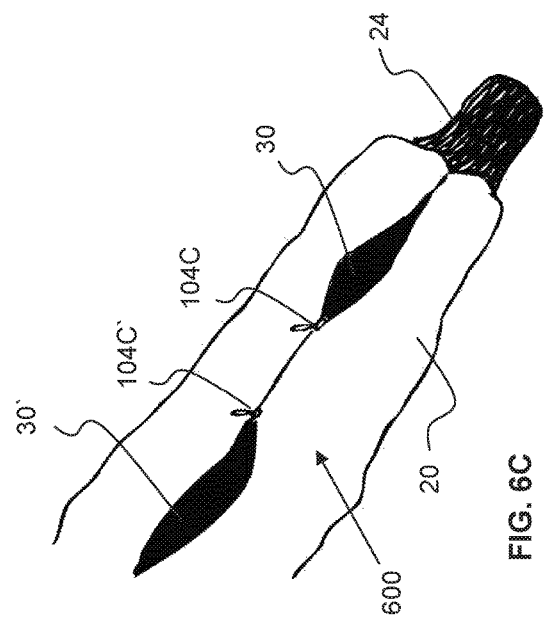

FIG. 6C depicts sleeve 20 with zipper 600 partially open in two areas. Near cuff 24 is a first opening 30 and near the shoulder end (not shown) is a second opening 30'. Opening 30 is revealed by drawing slider 104C away from the cuff end (as depicted in FIG. 6B). Opening 30' is revealed by drawing slider 104C' away from the shoulder end of the sleeve.

With the advent of more and more wearable electronics as well as the concealing of more and more devices and tools on the body, it is recognized that having clear and easy access to different portions of a covered arm is very useful. For example, iPod™ and iPhone™ arm straps are regularly used by joggers who wish to listen to audio media while exercising. Often times a jogger starts a jog early in the morning with a light windbreaker on against the cold and later removed the jacket during the course of the run when the temperature and/or body heats up. In such a case it is not practical to use iPod strap on the upper arm because there is no clear access to the device. On the other hand, strapping the device over the sleeve also has the drawback of having to fiddle with the strap when removing the jacket. Other electronic wearable devices may need to be in contact with the skin of the wearer in order to sense various body function indications such as pulse, temperature and blood pressure. Additional applications of the zipper sleeves, in various, configurations, present themselves on an almost daily basis.

In various professions and groups, members wear uniforms. In some of these groups such as mechanics, divers and various wings of the armed forces, the uniform is some version of a full body overall. It would be highly useful to have zipper, or other joining means (discussed immediately below) that can allow heretofore unavailable access to the wearer's arms. In the armed forces (as well as in civilian security contractors and even private individuals), for example, specialized suits and uniforms can benefit from the types of seams that can be opened and closed at will (as discussed at length in this document), in order to provide access to concealed weapons and other gear.

The common practice for paramedics, in emergency situations, is to cut open clothing in order to get access to the patient body. An expensive suit with a zipper seam of the immediate invention, or similar part-able seam, allows a medical professional to access the arm (e.g. to insert an I.V. or take blood pressure) without ruining the suit.

In an alternative configuration, the seam of FIG. 6A may include not a zipper but rather by another type of fabric fastener, such as one or more strips of a hook and loop fastener such as, but not limited to, VELCRO® brad hook-and-loop fastener. VELCRO® is a registered trademark of Velcro Industries B. V. Alternatively or additionally, the seam may include press studs, buttons or any other means of fastening two folds of fabric together, or any combinations of the above (including zippers of any kind). E.g. the seam from the armscye to the cuff may be made up of a zipper which runs a partial length of the sleeve, a hook and loop fastener which runs a partial length of the sleeve and terminating in one or more press studs near the cuff.

FIG. 6D depicts sleeve 20 with zipper 600 completely open. First slider 104C is drawn all the way across the zipper to abut second slider 104C'. Second slider 104C' is in a closed position, drawn all the way up to the top stops 102C (not shown distinctly) which are proximate to shoulder end 26. The seam loin 114U at the shoulder end, can be about one centimeter in length or about two centimeters in length or about three centimeters in length. The seam join (sewn portion) 114U at the shoulder end depicted in the figure is about three centimeters in length. Likewise, the seam join 114L at the cuff end, can be about one centimeter in length or about two centimeters in length or about three centimeters in length. The seam join (sewn portion) 114L at the cuff end depicted in the figure is about three centimeters in length. With the tail-to-tail configuration of the zipper 600, the zipper can be opened from shoulder end to cuff end (partially or fully), from cuff end to shoulder end (partially or fully), or both near the cuff and near the shoulder end.

Figure 7:
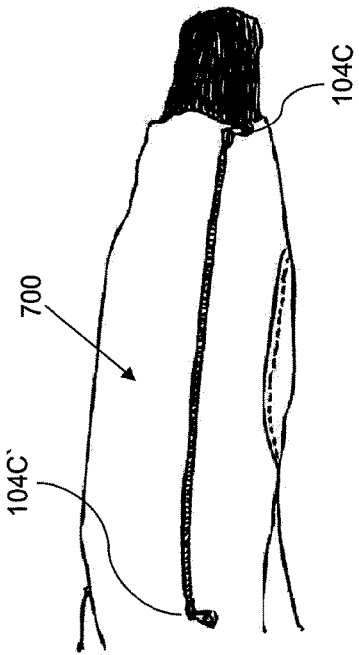
FIG. 7 is an exemplary jacket sleeve with a visible type zipper.

Yet another configuration is shown in FIG. 7. FIG. 7 depicts an exemplary jacket sleeve with a visible type zipper 700 having a first slider 104C and a second slider 104C' arranged in a tail-to-tail configuration and in a completely closed state.

Figure 8:
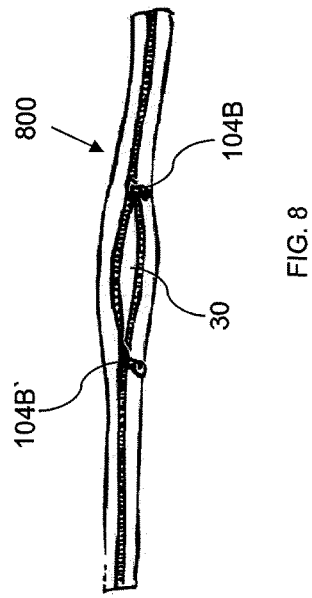
FIG. 8 is an exemplary visible type zipper.

FIG. 8 depicts an exemplary visible type zipper 800 having a first slider 104B and a second slider 104B' arranged in a head-to-head configuration and having a partial opening 30 midway along the zipper.

Figure 9:
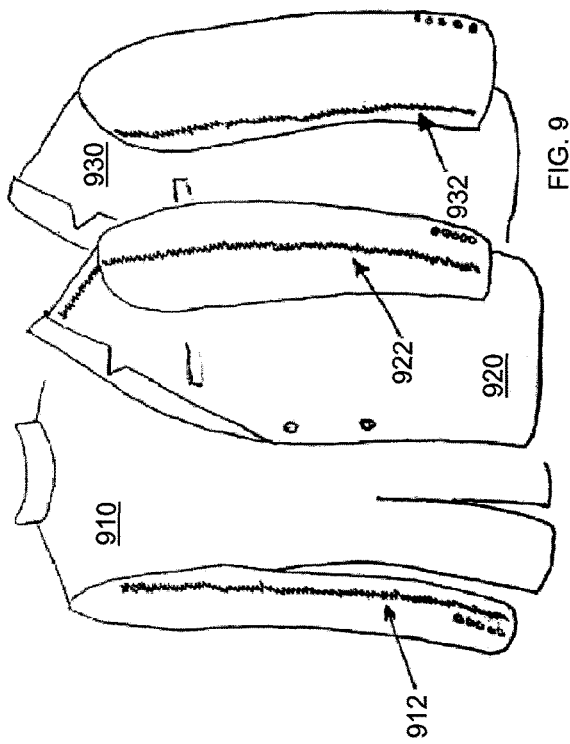
FIG. 9 depicts three partially visible suit jackets.

FIG. 9 depicts three partially visible suit jackets 910, 920 and 930. The partial view of jacket 910 is a back view of the jacket including the left sleeve. A zipper 912 is running down the back length of the sleeve. This position is different from the aforementioned zippers which run from the area of the armpit to the area of the wrist, on the palm side.

Suit jacket 920 is viewed in profile with a zipper 922 running down the middle of the sleeve as viewed in profile. Furthermore, the zipper extends up the shoulder piece and terminated prior to reaching the collar.

Suit jacket 930 is viewed in profile with a zipper 932 running down the front of the suit sleeve, from shoulder to cuff.

While the invention has been described with respect to a limited number of embodiments, it will be appreciated that many variations, modifications and other applications of the invention may be made. In particular, each of the various configurations discussed above may include hook-and-loop fasteners, buttons, press to studs and/or fabric fasteners of any kind in place of, or in addition to, the zippers discussed above. Therefore, the claimed invention as recited in the claims that follow is not limited to the embodiments described herein.

What is claimed is:

1. A garment having a garment sleeve and a shoulder portion, the garment sleeve having a proximal and shoulder end coupled to an armscye of the shoulder portion of the garment, and a distal cuff end terminating at a cuff of the garment sleeve, the garment sleeve comprising: a garment seam running from the proximal shoulder end to the cuff, said garment seam includes a first sewn portion proximal to the armscye and a second sewn portion proximal to the cuff; and
   a non-separating zipper extends continuously from said first sewn portion to said second sewn portion proximal to the cuff;
   said non-separating zipper including: teeth, at least one slider adapted to reversibly couple, at least partially, said teeth between said shoulder end and said cuff end to reversibly provide a passable aperture in said garment seam of the garment sleeve for wearer's arm to pass through said aperture when said garment sleeve is worn, and a tab, coupled to said at least one slider, wherein in a closed state said tab is adapted to be hidden in recesses of fabric of the garment;
   wherein said non-separating zipper is an invisible zipper, such that when said non-separating zipper is invisible in the closed state, and the garment sleeve appears to have a single contiguous sewn seam from the armscye to the cuff;
   wherein said garment seam runs from an area of the armpit to an area of a palm side of a wrist of wearer when the garment sleeve is worn; or
   wherein the garment sleeve is viewed in profile said garment seam runs down a front of the garment sleeve or a back length of the garment sleeve.

2. The garment of claim 1, further comprising a second slider, said second slider, in conjunction with said at least one slider adapted to reversibly open at least a portion of said non-separating zipper.

3. The garment of claim 2, wherein said at least one slider and said second slider are arranged in a head-to-head configuration on said non-separating zipper.

4. The garment of claim 2, wherein said at least one slider and said second slider are arranged in a tail-to-tail configuration on said non-separating zipper.

5. The garment of claim 1, wherein said sewn portion at said shoulder end abuts the armscye.

6. The garment of claim 1, wherein said sewn portion at said shoulder end, is a length selected from the group including: about one centimeter, about two centimeters and about three centimeters.

7. The garment of claim 1, wherein said sewn portion at said cuff end is of a length selected from the group including: less than one centimeter, about one centimeter, about two centimeters and about three centimeters.

8. The garment of claim 1, wherein said tab having a body length of about one centimeter.

9. A garment having a garment sleeve and a shoulder portion, the garment sleeve having a proximal, shoulder end coupled to an armscye of the shoulder portion of the garment, and a distal cuff end terminating at a cuff, the garment sleeve comprising:
   a garment seam running from the proximal shoulder end to the cuff, said garment seam including a sewn portion at said shoulder end and a sewn portion at said cuff end; and a non-separating fabric fastener operationally coupled to said sewn portion at shoulder end on one end thereof and to said sewn portion of said cuff end on a second end of said fabric fastener, said fabric fastener adapted to be unfastened and refastened to reversibly provide a passable aperture in said garment seam of the garment sleeve for user's arm to pass through said aperture when said garment sleeve is worn on said arm;
   wherein said non-separating fabric fastener is an invisible fabric fastener, such that said non-separating fabric fastener is invisible in a closed state, and the garment sleeve appears to have a single contiguous sewn seam from the armscye to the cuff;
   wherein said garment seam runs from an area of the armpit to an area of a palm side of a wrist when the garment sleeve is worn or wherein the garment sleeve is viewed in profiled said garment seam runs down a front of the garment sleeve or back length of the garment sleeve.

10. The garment of claim 9, wherein said fabric fastener is selected from one of: a zipper, a hook-and-loop fastener, press studs, buttons, clips and any combination thereof.

11. A garment having a sleeve, shoulder, a front panel and back panel and collar, the garment comprising:
    a garment seam running from the collar to a cuff of the sleeve, said garment seam comprises a first sewn portion proximal to the collar and a second sewn portion proximal to the cuff and an opening extending from said first sewn portion to said second sewn portion; and a fabric fastener extends continuously from said first sewn portion to said second sewn portion,
    said fabric fastener is adapted to be unfastened and refastened, thereby reversibly provide said opening with a passable aperture in said garment seam, wherein said fabric fastener is closed in by material on both ends thereof: and
    wherein the sleeve is viewed in profile with said fabric fastener running down a middle of the sleeve, and extending up and over the shoulder of the garment and terminating prior to reaching the collar of the garment;
    wherein said fabric fastener is an invisible fabric fastener, such that when said invisible fabric fastener is in a closed state, the garment sleeve appears to have a single contiguous sewn seam from the to the cuff.

12. The garment of claim 11, wherein said fabric fastener is a non-separating zipper.

13. The garment of claim 12, wherein said non-separating zipper comprises teeth, a first slider and a second slider, said second slider, in conjunction with said first slider are adapted to reversibly open at least a portion of said non-separating zipper.

\* \* \* \* \*